United States Patent [19]
Petroff et al.

[11] Patent Number: 5,981,680
[45] Date of Patent: Nov. 9, 1999

[54] METHOD OF MAKING SILOXANE-BASED POLYAMIDES

[75] Inventors: Lenin James Petroff, Bay City; Jay Brian Rose; Michael Ward Skinner, both of Midland, all of Mich.

[73] Assignee: Dow Corning Corporation, Midland, Mich.

[21] Appl. No.: 09/114,381

[22] Filed: Jul. 13, 1998

[51] Int. Cl.$^6$ .................................................. C08G 77/26
[52] U.S. Cl. ................................. 528/26; 528/15; 528/31
[58] Field of Search .................... 528/26, 15, 31

[56] References Cited

U.S. PATENT DOCUMENTS

| | | | |
|---|---|---|---|
| 3,218,344 | 11/1965 | Bailey | 528/15 |
| 3,313,773 | 4/1967 | Lamoreaux | 528/26 |
| 3,392,143 | 7/1968 | Holub | 528/26 |
| 3,746,738 | 7/1973 | Pepe et al. | 528/26 |
| 3,892,643 | 7/1975 | Tanaka et al. | 528/15 |
| 4,145,508 | 3/1979 | Bargain et al. | 528/31 |
| 5,874,069 | 2/1999 | Mendolia et al. | 424/65 |

*Primary Examiner*—Margaret G. Moore
*Attorney, Agent, or Firm*—James L. De Cesare

[57] ABSTRACT

A method of making siloxane-based polyamides which includes at least one repeating unit represented by the formula

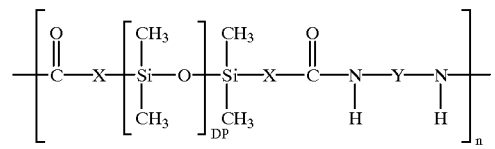

wherein X is a linear or branched $C_1$–$C_{30}$ alkylene chain; Y is a linear or branched $C_1$–$C_{20}$ alkylene chain; DP is an integer having a value of 10–500; n is an integer having a value of 1–500. The method involves heating an intimate reaction mixture containing an olefinic acid and an organic diamine at a temperature greater than 100° C. and forming an organic diamide; and thereafter reacting the organic diamide with a hydride-terminated polydimethylsiloxane in the presence of a hydrosilylation catalyst to form the siloxane-based polyamide.

10 Claims, No Drawings

METHOD OF MAKING SILOXANE-BASED POLYAMIDES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to an improvement in the method of making siloxane-based polyamides described in a prior copending application, U.S. Ser. No. 08/904,709, filed Aug. 1, 1997, and entitled "Cosmetic Composition Containing Siloxane-Based Polyamides as Thickening Agents", hereafter referred to as the '709 application.

BACKGROUND OF THE INVENTION

The present invention relates to a novel method of making siloxane-based polyamides.

There is a growing demand in the personal care arena for polymeric materials capable of thickening dimethylcyclosiloxanes in order to modify product viscosity in various market niche hair, skin, cosmetic, and underarm, applications.

The '709 application is directed to one type of a process for preparing siloxane-based polyamides. The process according to the '709 application involves many steps, and this results in cost prohibitive products which are difficult to produce in commercial quantity.

For example, in the '709 application process, a dimethyl hydride endblocked polydimethylsiloxane is first prepared containing the appropriate number of siloxane units to achieve a desired value of DP. The carboxylic acid group of undecylenic acid is then protected through reaction with hexamethyldisilazane. The dimethyl hydride endblocked polydimethylsiloxane and the protected undecylenic acid are reacted to produce a siloxane diacid, i.e., a carboxydecyl terminated polydimethylsiloxane. This reaction is accomplished in the presence of a platinum catalyst, and the product is washed with methanol to remove the trimethylsilyl protecting group from the protected siloxane diacid. The siloxane diacid is then reacted with an organic diamine to produce a siloxane-based polyamide.

Accordingly, a new process has been discovered herein that eliminates many of the otherwise costly steps involved in the process according to the '709 application.

The new process basically involves the addition of an olefinic acid with an organic diamine to produce an organic diamide. Once the olefinic acid and the organic diamine are fully reacted, an $\equiv$SiH endblocked polysiloxane is added in the presence of a platinum catalyst, to produce a siloxane-based polyamide via hydrosilylation. The resulting polymeric product is in the form of a high molecular weight thermoplastic polymer. The benefits of this process is that it allows for the production of a cost effective manufactured product in commercial quantity.

BRIEF SUMMARY OF THE INVENTION

This invention relates to a method of forming siloxane-based polyamides which are useful as thickening agents to formulate a wide variety of cosmetic compositions. The polyamides of this invention are multiples of a unit represented by the following Formula A:

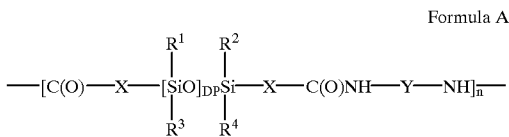

Formula A where:

(1) The degree of polymerization (DP) is 1–700, preferably 10–500, and more preferably 15–45. DP represents an average value for degree of polymerization of the siloxane units in the polymer with greater or lesser DP values centered around the indicated DP value.

(2) n is 1–500, particularly 1–100, and more particularly 4–25.

(3) X is a linear or branched chain alkylene having 1–30 carbons, particularly 3–10 carbons, and more particularly 10 carbons.

(4) Y is a linear or branched chain alkylene having 1–40 carbons, particularly 1–20 carbons, more particularly 2–6 carbons, and especially 6 carbons wherein (a) The alkylene group may optionally and additionally contain in the alkylene portion at least one of (i) 1–3 amide linkages; (ii) a C5 or C6 cycloalkane; or (iii) phenylene, optionally substituted by 1–3 members which are independently C1–C3 alkyls; and (b) the alkylene group itself may optionally be substituted by at least one of (i) hydroxy; (ii) a C3–C8 cycloalkane; (iii) 1–3 members which are independently C1–C3 alkyls; phenyl, optionally substituted by 1–3 members which are independently C1–C3 alkyls; (iv) a C1–C3 alkyl hydroxy; or (v) a C1–C6 alkyl amine; and (c) Y can be Z where Z is $T(R^{20})(R^{21})(R^{22})$ where $R^{20}$, $R^{21}$ and $R^{22}$ are each independently linear or branched C1–C 10 alkylenes; and T is CR in which R is hydrogen, the group defined for $R^1$–$R^4$, or a trivalent atom such as N, P and Al.

(5) Each of $R^1$–$R^4$ (collectively "R") is independently methyl, ethyl, propyl, isopropyl, a siloxane chain, or phenyl, wherein the phenyl may optionally be substituted by 1–3 members which are methyl or ethyl. More particularly, $R^1$–$R^4$ are methyl or ethyl, especially methyl.

(6) X, Y, DP, and $R^1$–$R^4$ may be the same or different for each polyamide unit.

By "siloxane chain" is meant a group of units such as:

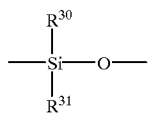

where $R^{30}$ and $R^{31}$ are each independently organic moieties; and each $R^{30}$ and $R^{31}$ are connected to silicon by a carbon-silicon bond.

The carbon numbers in the alkylene chain do not include the carbons in the extra segments or substitutions. Also, the polyamides must have a siloxane portion in the backbone and optionally may have a siloxane portion in a pendant or branched portion.

If repeated with no variations in the defined variables, Formula A is representative of a linear homopolymer. Variations of the invention include: (1) polyamides in which multiple values of DP, and of units X, Y, and $R^1$–$R^4$ occur in one polymeric molecule, and wherein the sequencing of these units may be alternating, random or block; (2) polyamides in which an organic triamine or higher amine such as tris(2-aminoethyl)amine replaces the organic diamine in part, to produce a branched or crosslinked molecule; and (3) physical blends of any of (1) and (2) and/or linear homopolymers.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

This invention is directed to a new and novel process for making siloxane-based polyamides. As it relates to the '709 application, the process eliminates costly steps and produces a polymer with higher molecular weights than achieved with the previous process in the '709 application. For example, average molecular weights as measured by gel permeation chromatography (GPC), using the process according to the '709 application were determined to be approximately 50,000. The new process according to the present invention produces average molecular weights of approximately 65,000.

In addition, the process according to this invention is much faster than the particular process of the '709 application as well as other traditional processes for making siloxane-based polyamides. The '709 application process takes approximately four days to make a finished siloxane-based polyamide polymer, while the new route according to the present invention takes approximately one day. The thermoplastic polymer produced as a result of the instant process is ideal for the thickening of dimethylcyclosiloxanes, which renders it of benefit in a large number of personal care product applications.

Basically, the new process involves the addition of an olefinic acid such as undecylenic acid $H_2C=CH(CH_2)_8COOH$ to an organic diamine such as hexamethylene diamine $H_2N(CH_2)_6NH_2$, to produce an organic diamide. This organic diamide product is then reacted with an $\equiv SiH$ endblocked polysiloxane in the presence of a platinum catalyst to produce the siloxane-based polyamide. Analysis using GPC confirm and indicate the achievement of high molecular weight growth using the process according to the present invention.

Some examples of compounds of Formula A include:

1) Polyamides of Formula I:

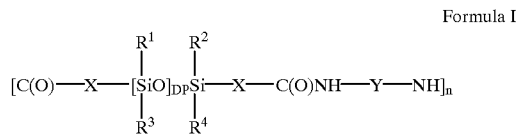

Formula I where X, Y, n, $R^1$–$R^4$, and DP are as defined for Formula A. A particular subgroup of Formula I are compounds where $R^1$, $R^2$, $R^3$ and $R^4$ are each methyl. Preferred polyamides of Formula I are:

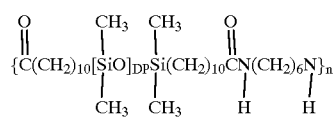

where DP is 10–500, particularly 15–45, and more particularly 29. Another particular group contains polyamides of Formula I where X, Y, DP and $R^1$–$R^4$ are the same in each unit of the polymer.

2) Polyamides containing multiple siloxane block lengths as shown in Formula II:

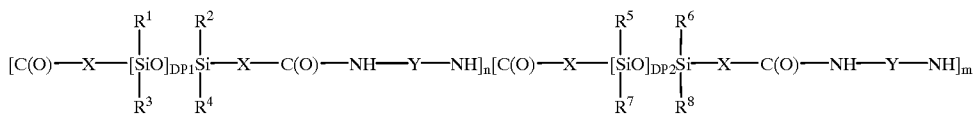

Formula II where X, Y, n, and $R^1$–$R^4$ have the meanings described above for Formula A; m is the same as the value defined for n; and n and m denote the total number of units enclosed within the brackets; with the individual units arranged with regular, alternating, block, or random sequencing.

$R^5$–$R^8$ is the same group as defined for $R^1$–$R^4$; DP1 and DP2 may be the same or different, and each can be independently the same as defined for DP. The units denominated by n and m may be structured to form either block (regularly sequenced) or random copolymers.

A particular subgroup for compounds of Formula II may have methyl for all R groups. Another particular subgroup of compounds of Formula II may have DP1 equal to DP2. A third particular subgroup may have methyl for all R groups, and DP1 equal to DP2.

3) Polyamides synthesized from multiple diamines as shown in Formula III:

where X, Y, $Y^1$, $R^1$–$R^8$, m, n, DP1, and DP2, are the same as defined above; $R^9$–$R^{12}$ are the same as defined for $R^1$–$R^8$; DP3 is the same as defined for DP; p is the same as defined for m and n; Z is $T(R^{20})(R^{21})(R^{22})$ where $R^{20}$, $R^{21}$ and $R^{22}$ are each independently linear or branched C1–C10 alkylenes; and T is CR where R is hydrogen, the same as defined for $R^1$–$R^4$, or a trivalent atom such as N, P and Al.

Preferred values for p are 1–25, with more preferred values being 1–7. Preferred units for $R^1$–$R^{12}$ are methyl. T is preferably N. Particular values for DP1 to DP3 are 10–500, and more particularly 15–45. $R^{20}$, $R^{21}$, and $R^{22}$ are preferably ethylene. A preferred group representative of Z is $(-CH_2CH_2)_3N$.

One particular group of compounds of Formula IV is represented by the formula

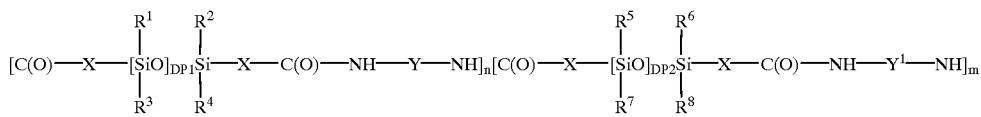

Formula III where X, Y, m, n, $R^1$–$R^8$, DP1, DP2 have the same meanings as described above for Formula A and Formula II; $Y^1$ is independently selected from the same group as defined for Y; and the units denominated by n and m may be structured to form either block (regularly sequenced) or random copolymers.

A particular subgroup of compounds of Formula III may have DP1 equal to DP2. Another particular subgroup of compounds of Formula III may have methyl for all R groups. A third particular subgroup may have methyl for all R groups, and DP1 equal to DP2.

4) Polyamides synthesized with a trifunctional amine as shown in Formula IV:

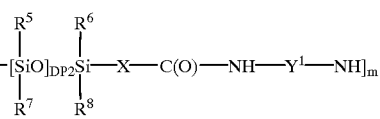

Formula IV

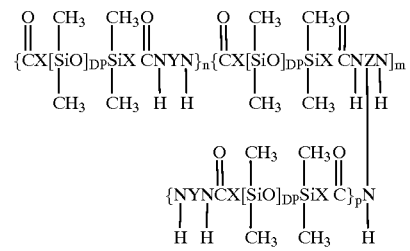

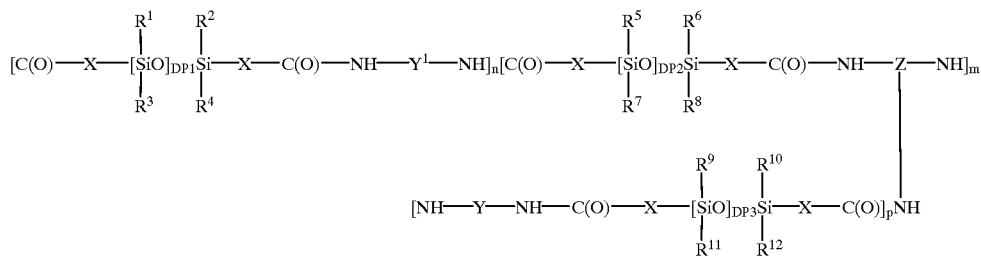

Formula IV where X is —(CH$_2$)$_{10}$—, Y is —(CH$_2$)—; DP is 15–45; m is 5–20% of n+p; and Z is (—CH$_2$CH$_2$)$_3$N.

Siloxane-based polyamides according to this invention (1) contain both siloxane groups and amide groups which facilitate the thickening of compositions containing volatile silicone fluids and non-volatile silicone fluids; (2) are non-flowable solids at room temperature; and (3) dissolve in a fluid which contains silicone at a temperature of 25–160° C., to form translucent or clear solutions at a temperature in this range.

With regard to the siloxane units in the siloxane-based polyamides, the siloxane units must be in the main or backbone chain but can also optionally be present in branched or pendent chains. In the main chain the siloxane units occur in segments as described above. In the branched or pendent chains the siloxane units can occur individually or in segments.

Particular groups of siloxane-based polyamides include:
(a) polyamides of Formula I where the DP is 15–50;
(b) physical blends of two or more polyamides wherein at least one polyamide has a value for DP in the range of 15–50, and at least one polyamide has a value for DP in the range of 30–500;
(c) compounds of Formula II where (1) the value for DP1 is 15–50, and the value for DP2 is 30–500; and (2) the portion of the polyamide having DP1 is about 1–99 weight % based on the weight of the total polyamide content, and the portion of the polyamide having DP2 is about 1–99 weight %;
(d) physical blends of polyamides of Formula I made by combining (1) 80–99 weight % of a polyamide where n is 2–10, and especially where n is 3–6; and (2) 1–20 weight % of a polyamide where n is 5–500, especially where n is 6–100;
(e) polyamides of Formula III where at least one Y or Y$^1$ contains at least one hydroxyl substitution;
(f) polyamides of Formula A synthesized with at least a portion of an activated diacid, such as a diacid chloride, dianhydride, or diester, instead of the diacid;
(g) polyamides of Formula A where X is —(CH$_2$)$_3$—; and
(h) polyamides of Formula A where X is —(CH$_2$)$_{10}$—.

THE PROCESS ACCORDING TO THE '709 APPLICATION

A reaction scheme for making polyamides of Formula I according to the '709 application involves the condensation of a siloxane diacid with an organic diamine as shown below.

(1) A dimethyl hydride endblocked polydimethylsiloxane, such as one of the type shown below, is prepared containing the appropriate number of siloxane units "n" to achieve the desired value of DP.

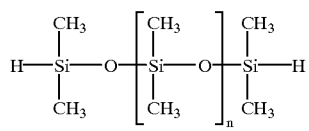

(2) The carboxylic acid group of undecylenic acid is protected through reaction with hexamethyldisilazane (CH$_3$)$_3$—Si—NH—Si—(CH$_3$)$_3$. This step is shown below.

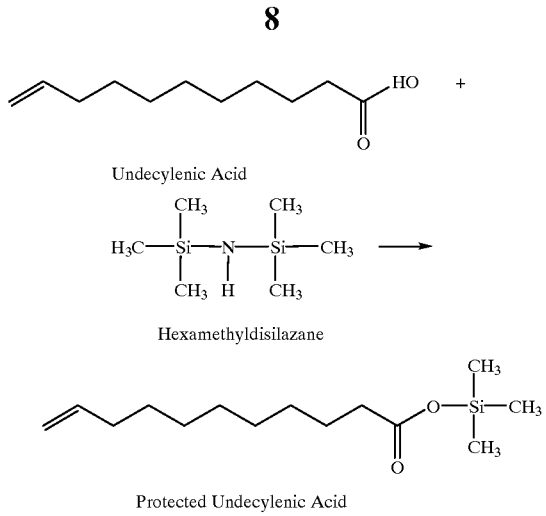

(3) The dimethyl hydride endblocked polydimethylsiloxane and the protected undecylenic acid (the products of Steps (1) and (2)) are reacted to produce a siloxane diacid (carboxydecyl terminated polydimethylsiloxane). This reaction is accomplished in the presence of a platinum catalyst such as chloroplatinic acid, and the product is washed with methanol to remove the trimethylsilyl protecting group from the protected siloxane diacid shown below.

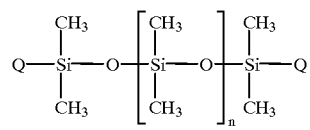

where Q is

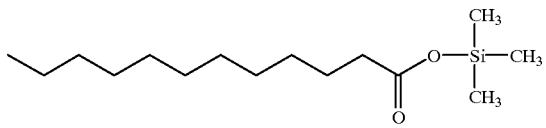

(4) The siloxane diacid (product of Step (3)) is reacted with an organic diamine to produce a siloxane-based polyamide. The siloxane diacid is shown below. This reaction may involve the use of a reaction solvent such as toluene or xylene.

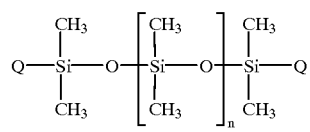

where Q is

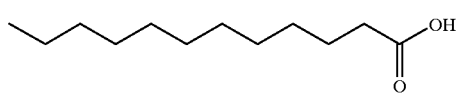

THE PROCESS ACCORDING TO THE PRESENT INVENTION

The simplified process of the present invention can be illustrated schematically with reference to the following reaction scenario in which an olefinic acid is reacted with an organic diamine to produce an organic diamide.

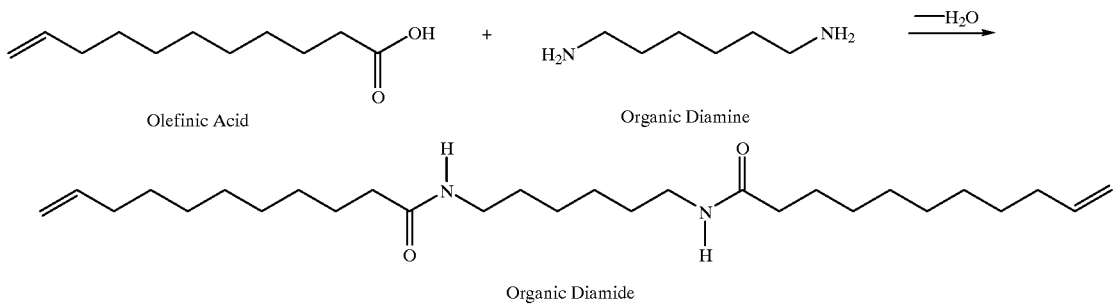

Olefinic Acid    Organic Diamine

Organic Diamide

The organic diamide is then in turn reacted with a hydride-terminated polydimethylsiloxane of the structure such as the one depicted below:

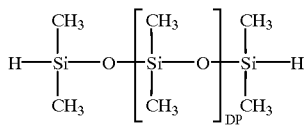

in the presence of a hydrosilylation catalyst to form a siloxane-based polyamide which includes at least one repeating unit represented by the formula

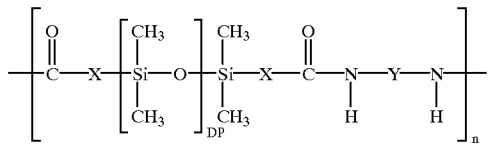

wherein X is a linear or branched $C_1$–$C_{30}$ alkylene chain; Y is a linear or branched $C_1$–$C_{20}$ alkylene chain; DP is an integer having a value of 10–500; n is an integer having a value of 1–500.

Suitable olefinic acids which can be used include undecylenic acid $H_2C=CH(CH_2)_8COOH$, acrylic acid $H_2C=CHCOOH$, 3-butenoic acid (vinylacetic acid) $H_2C=CHCH_2COOH$, 4-pentenoic acid $H_2C=CHCH_2CH_2COOH$, and other olefinic acids with carbon chains of varying length.

Organic amines which can be used herein preferably include linear alkyl diamines such as hexamethylene diamine, ethylene diamine, and mixtures of linear alkyl diamines, as well as other amines such as decamethylene diamine.

A platinum catalyzed hydrosilylation reaction is employed according to this invention. Generally, hydrosilylation involves the reaction between a polysiloxane containing ≡Si—H groups, and a material containing unsaturation, e.g., vinyl groups. Some attractive features of this mechanism are that no by-products are formed, and hydrosilylation will proceed even at room temperature. In the mechanism, crosslinking involves addition of ≡SiH across double bonds, i.e.,

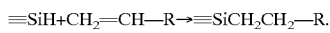

The process requires a catalyst to effect the reaction between the ≡SiH containing polysiloxane and the material containing unsaturation, i.e., the organic diamide in the case of the present invention. Suitable catalysts are Group VIII transition metals, i.e., the noble metals. Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing about one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

The noble metal catalyst can be used in an amount of from 0.00001–0.5 parts per 100 weight parts of the ≡SiH containing polysiloxane. Preferably, the catalyst should be used in an amount sufficient to provide 5–15 parts per million (ppm) Pt metal per total composition.

Carrying out of the process is simply a matter of combining the ≡SiH containing polysiloxane(s), the material containing unsaturation, i.e., the organic diamide, and the catalyst; and mixing these ingredients. The reaction temperature can vary over a wide range, and the optimum temperature is dependent upon the concentration of the catalyst and the nature of the reactants. Ordinarily, it is best to keep the reaction temperature below about 300° C. Best results with most reactants can be obtained by initiating the reaction at about 80° C. to 180° C., and maintaining the reaction within reasonable limits of this range.

Typically, the process is carried out using approximately a 1:1 molar ratio of ≡Si—H containing polysiloxane and the material containing unsaturation. It is expected that useful materials may also be prepared by carrying out the process with an excess of either the ≡Si—H containing polysiloxane or the material containing unsaturation, but this would be considered a less efficient use of the materials.

The process can also be used to make other types of siloxane-based polyamides in which the repeating unit of the siloxane-based polyamide is represented by the formula

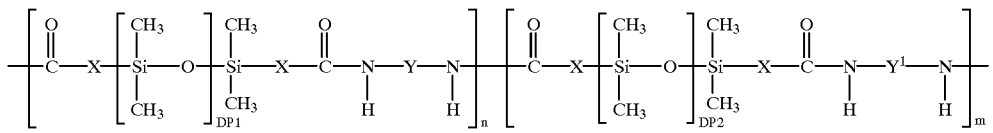

or by the formula

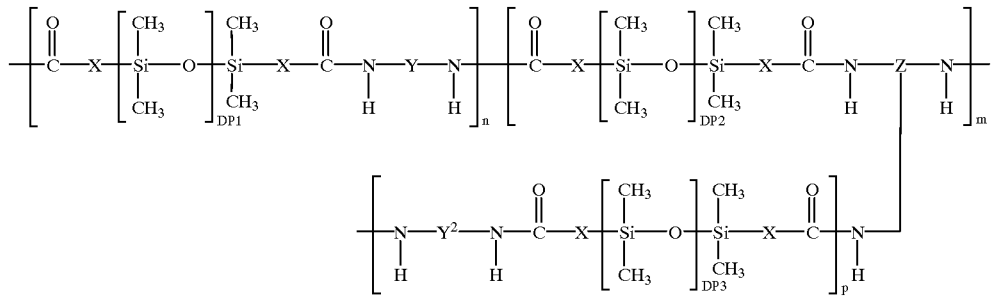

wherein X is a linear or branched $C_1$–$C_{30}$ alkylene chain; Y, $Y^1$, and $Y^2$ are linear or branched $C_1$–$C_{20}$ alkylene chains; DP1, DP2, and DP3 are integers each having values of 10–500; n, m, and p are integers each having values of 1–500; Z is represented by

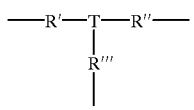

wherein R', R", and R'" are linear or branched $C_1$–$C_{10}$ alkylene groups; and T is CR in which R is hydrogen, methyl, ethyl, propyl, isopropyl, a siloxane chain, or phenyl, wherein the phenyl may optionally be substituted by 1–3 members which are methyl or ethyl, or T is a trivalent atom such as N, P and Al; provided n is not the same as m, or Y is not the same as $Y^1$, or DP1 is not the same as DP2.

EXAMPLES

Following are specific synthesis examples for forming siloxane-based polyamides according to the method of this invention. Unless otherwise indicated, the vacuums described in Examples 1–4 are in the range of 5–20 millimeters of mercury. While particular siloxane-based polyamides are disclosed or used in the following Examples, it is to be understood that other siloxane-based polyamides, for example, those made with a purified siloxane diacid, dianhydride, diester, or diacid chloride, may also be used.

Example 1
30 DP Polymer

A 500 ml three neck flask equipped with a thermometer, electrical stirrer, nitrogen sweep, and a condenser, was charged with 50.12 g of undecylenic acid, and 22.58 g of a 70% hexamethylene diamine mixture in water. The flask was immediately heated to 225 degrees C. and kept at this temperature for 2 hours. After 2 hours, a vacuum was applied to the system for 2 hours to remove any unreacted materials. Upon completion of vacuum stripping, the flask was reweighed to obtain the product weight. The temperature was increased to 120 degrees C., and 65 g of toluene, and 0.5 g of a solution containing platinum in the form of a complex of platinous chloride and divinyl tetramethyl disiloxane, were added to the flask. The temperature was increased to 185 degrees C., and 279.2 g of a 30 DP dimethylhydrogen endblocked polydimethylsiloxane was added to the flask over a 30 minute period. After complete addition, a dean stark trap was used to replace the addition funnel on the flask, and the toluene was removed from the flask. After removal of the toluene, the materials were allowed to react for an additional period of one hour. Vacuum stripping was applied to the flask for 1 hour to ensure complete removal of any residual solvent. The temperature of the final siloxane-based polyamide was cooled to 150° C. and poured off while still in the melt form.

Example 2
20 DP Polymer

A 500 ml three neck flask equipped with a thermometer, electrical stirrer, nitrogen sweep, and a condenser, was charged with 55.0 g of undecylenic acid, and 24.77 g of a 70% hexamethylene diamine mixture in water. The flask was immediately heated to 225 degrees C., and kept at this temperature for 2 hours. After 2 hours, a vacuum was applied to the system for 2 hour to remove any unreacted materials. Upon completion of vacuum stripping, the flask was reweighed to obtain the product weight. The temperature controller was increased to 120 degrees C., and 65 g of toluene, and 0.5 g of a solution containing platinum in the form of a complex of platinous chloride and divinyl tetramethyl disiloxane, were added to the flask. The temperature was then increased to 185 degrees C., and 222.0 g of a 20 DP dimethylhydrogen endblocked polydimethylsiloxane was added to the flask over a 30 minute period. After complete addition, a dean stark trap was used to replace the addition funnel on the flask, and the toluene was removed from the flask. After removal of the toluene, the materials were allowed to react for an additional period of one hour. Vacuum stripping was applied to the flask for 1 hour to ensure complete removal of any residual solvent. The temperature of the final siloxane-based polyamide was cooled to 150° C. and poured off while still in the melt form.

Example 3
15 DP Polymer

A 500 ml three neck flask equipped with a thermometer, electrical stirrer, nitrogen sweep, and a condenser, was charged with 57.75 g of undecylenic acid, and 24.77 g of a 70% hexamethylene diamine mixture in water. The flask was immediately heated to 225 degrees C., and kept at this temperature for 2 hours. After 2 hours, a vacuum was applied to the system for 2 hours to remove any unreacted materials. Upon completion of vacuum stripping, the flask was reweighed to obtain the product weight. The temperature was increased to 120 degrees C., and 65 g of toluene, and 0.5 g of a solution containing platinum in the form of a complex of platinous chloride and divinyl tetramethyl disiloxane were added to the flask. The temperature was then increased to 185 degrees C., and 168.72 g of a 15 DP dimethylhydrogen endblocked polydimethylsiloxane was added to the flask over a 30 minute period. After complete addition, a dean stark trap was used to replace the addition funnel on the flask, and the toluene was removed from the flask. After removal of the toluene, the materials were allowed to react for an additional period of one hour. Vacuum stripping was applied to the flask for 1 hour to ensure complete removal of any residual solvent. The temperature of the final siloxane-based polyamide was cooled to 150° C. and poured off while still in the melt form.

Example 4
10 DP Polymer

A 500 ml three neck flask equipped with a thermometer, electrical stirrer, nitrogen sweep, and a condenser, was charged with 67.0 g of undecylenic acid, and 29.82 g of a 70% hexamethylene diamine mixture in water. The flask was immediately heated to 225 degrees C., and kept at this temperature for 2 hours. After 2 hours, a vacuum was applied to the system for 2 hours to remove any unreacted materials. Upon completion of vacuum stripping, the flask was reweighed to obtain the product weight. The temperature was increased to 120 degrees C., and 65 g of toluene, and 0.5 g of a solution containing platinum in the form of a complex of platinous chloride and divinyl tetramethyl disiloxane, were added to the flask. The temperature was then increased to 185 degrees C., and 150.97 g of a 10 DP dimethylhydrogen endblocked polydimethylsiloxane was added to the flask over a 30 minute period. After complete addition, a dean stark trap was used to replace the addition funnel on the flask, and the toluene was removed from the flask. After removal of the toluene, the materials were allowed to react for an additional period of one hour. Vacuum stripping was applied to the flask for 1 hour to ensure complete removal of any residual solvent. The temperature of the final siloxane-based polyamide was cooled to 150° C. and poured off while still in the melt form.

Although undecylenic acid, acrylic acid, 3-butenoic acid (vinylacetic acid), and 4-pentenoic acid, have been set forth as being representative examples of some suitable olefinic acids, it should be understood that other branched or straight-chain alkenoic acids $C_nH_{(2n-2)}O_2$ can be employed in accordance with the method of the present invention.

The siloxane-based polyamides according to this present invention can be used as thickening agents in hair, skin, underarm, and cosmetic, product applications. The siloxane units provide compatibility with silicone fluids such as cyclomethicones, while the amide linkages and the spacing and selection of the locations of the amide linkages, facilitate thickening and formation of such products.

Other variations may be made in compounds, compositions, and methods described herein without departing from the essential features of the invention. The embodiments of the invention specifically illustrated herein are exemplary only and not intended as limitations on their scope except as defined in the appended claims.

I claim:

1. A method of making a siloxane-based polyamide which includes at least one repeating unit represented by the formula

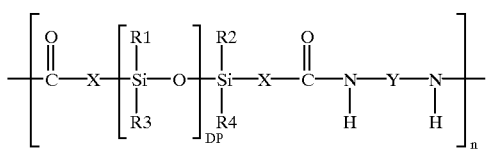

wherein X is a linear or branched $C_3$ to $C_{10}$ alkylene chain; Y is a linear or branched $C_1$–$C_{20}$ alkylene chain; $R^1$–$R^4$ are independently methyl, ethyl, propyl, isopropyl, a siloxane chain, phenyl, or phenyl substituted by 1–3 members which are methyl or ethyl; DP is an integer having a value of 10–500; and n is an integer having a value of 1–500;

the method comprising heating a reaction mixture containing an olefinic acid and an organic diamine at a temperature greater than 100° C. and forming an organic diamide; and thereafter reacting the organic diamide with a hydride-terminated polydimethylsiloxane in the presence of a hydrosilylation catalyst to form the siloxane-based polyamide.

2. A method according to claim 1 in which the organic diamine is a compound selected from the group consisting of hexamethylene diamine, ethylene diamine, and decamethylene diamine.

3. A method according to claim 1 in which the olefinic acid is a compound selected from the group consisting of undecylenic acid, acrylic acid, 3-butenoic acid, and 4-pentenoic acid.

4. A method according to claim 1 in which the siloxane-based polyamide has a number average molecular weight of from 4,000 to 200,000 daltons, as determined by gel permeation chromatography using polydimethylsiloxane as a standard.

5. A method according to claim 4 in which the siloxane-based polyamide has a number average molecular weight of from 5,000 to 65,000 daltons, as determined by gel permeation chromatography using polydimethylsiloxane as a standard.

6. A method according to claim 1 in which the repeating unit of the siloxane-based polyamide is represented by the formula

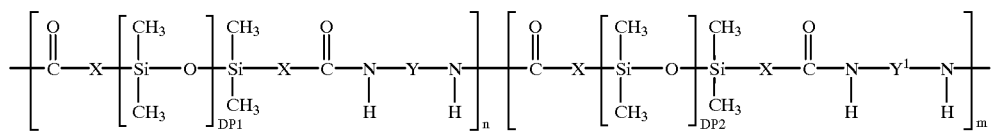

or the formula

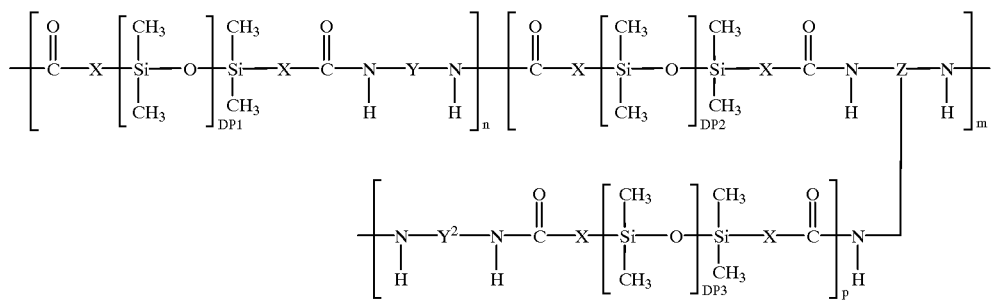

wherein X is a linear or branched $C_3$ to $C_{10}$ alkylene chain; Y, $Y^1$, and $Y^2$ are linear or branched $C_1$–$C_{20}$ alkylene chains; DP1, DP2, and DP3 are integers each having values of 10–500; n, m, and p are integers each having values of 1–500; Z is represented by

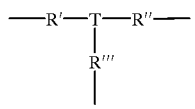

wherein R', R", and R'" are linear or branched $C_1$–$C_{10}$ alkylene groups; and T is CR in which R is hydrogen, methyl, ethyl, propyl, isopropyl, a siloxane chain, or phenyl, wherein the phenyl may optionally be substituted by 1–3 members which are methyl or ethyl, or T is a trivalent atom such as N, P and Al; provided n is not the same as m, or Y is not the same as $Y^1$, or DP1 is not the same as DP2.

7. A method of making a siloxane-based polyamide which includes at least one repeating unit represented by the formula

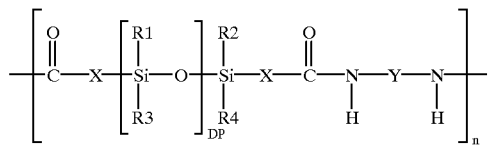

wherein X is a linear or branched $C_3$ to $C_{10}$ alkylene chain; Y is a linear or branched $C_1$–$C_{20}$ alkylene chain; $R^1$–$R^4$ are independently methyl, ethyl, propyl, isopropyl, a siloxane chain, phenyl, or phenyl substituted by 1–3 members which are methyl or ethyl; DP is an integer having a value of 10–500; and n is an integer having a value of 1–500;

the method comprising reacting an organic diamide with a hydride-terminated polydimethylsiloxane in the presence of a hydrosilylation catalyst to form the siloxane-based polyamide.

8. A method according to claim 7 in which the siloxane-based polyamide has a number average molecular weight of from 4,000 to 200,000 daltons, as determined by gel permeation chromatography using polydimethylsiloxane as a standard.

9. A method according to claim 8 in which the siloxane-based polyamide has a number average molecular weight of from 5,000 to 65,000 daltons, as determined by gel permeation chromatography using polydimethylsiloxane as a standard.

10. A method according to claim 7 in which the repeating unit of the siloxane-based polyamide is represented by the formula

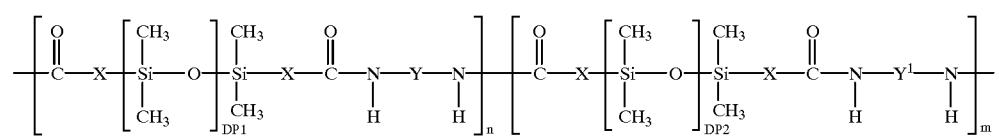

or the formula

-continued

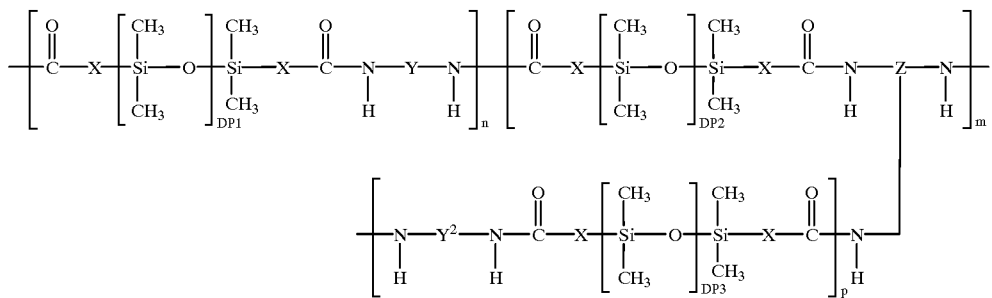

wherein X is a linear or branched $C_3$ to $C_{10}$ alkylene chain; Y, $Y^1$, and $Y^2$ are linear or branched $C_1$–$C_{20}$ alkylene chains; DP1, DP2, and DP3 are integers each having values of 10–500; n, m, and p are integers each having values of 1–500; Z is represented by

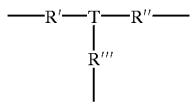

wherein R', R", and R'" are linear or branched $C_1$–$C_{10}$ alkylene groups; and T is CR in which R is hydrogen, methyl, ethyl, propyl, isopropyl, a siloxane chain, or phenyl, wherein the phenyl may optionally be substituted by 1–3 members which are methyl or ethyl, or T is a trivalent atom such as N, P and Al; provided n is not the same as m, or Y is not the same as $Y^1$, or DP1 is not the same as DP2.

* * * * *